US012646237B2

(12) United States Patent
Xing et al.

(10) Patent No.: US 12,646,237 B2
(45) Date of Patent: Jun. 2, 2026

(54) COMPUTED TOMOGRAPHY IMAGING METHOD AND APPARATUS

(71) Applicant: GE Precision Healthcare LLC, Waukesha, WI (US)

(72) Inventors: Weiwei Xing, Beijing (CN); Xueli Wang, Beijing (CN); Bingjie Zhao, Beijing (CN)

(73) Assignee: GE Precision Healthcare LLC, Waukesha, WI (US)

( * ) Notice: Subject to any disclaimer, the term of this patent is extended or adjusted under 35 U.S.C. 154(b) by 279 days.

(21) Appl. No.: 18/496,747

(22) Filed: Oct. 27, 2023

(65) Prior Publication Data

US 2024/0144556 A1 May 2, 2024

(30) Foreign Application Priority Data

Oct. 28, 2022 (CN) .......................... 202211333377.X

(51) Int. Cl.
G06T 12/10 (2026.01)
A61B 6/03 (2006.01)
A61B 6/50 (2024.01)

(52) U.S. Cl.
CPC .............. G06T 12/10 (2026.01); A61B 6/032 (2013.01); A61B 6/503 (2013.01); G06T 2211/428 (2013.01)

(58) Field of Classification Search
None
See application file for complete search history.

(56) References Cited

U.S. PATENT DOCUMENTS 6,385,278 B1    5/2002  Hsieh
6,529,576 B2 *  3/2003  Hsieh ..................... A61B 6/027
                                                             378/19

(Continued)

FOREIGN PATENT DOCUMENTS

CN        113298903 A      8/2021
CN        113520440 B      4/2024

(Continued)

OTHER PUBLICATIONS

Li et al., Strategy of computed tomography sinogram inpainting based on sinusoid-like curve decomposition and eigenvector-guided interpolation, J. Opt, Soc. Am. A, vol. 29, No. 1, pp. 153-164 (Year: 2012).*

*Primary Examiner* — Uzma Alam
*Assistant Examiner* — Djura Malevic

(57) ABSTRACT

Embodiments of the present application provide a computed tomography imaging method and apparatus. The method includes pre-scanning an examined site by using an incomplete detector at a pitch factor of greater than 3 to obtain first data, axially scanning the examined site using the incomplete detector to obtain second data, stitching the first data and the second data to obtain third data; compensating the third data to obtain compensated third data, and performing image reconstruction by using the compensated third data to obtain a scanned image. Therefore, by performing two scans using an incomplete detector, stitching and compensating data obtained by the two scans, while reducing the total dose of X-rays, the integrity of the obtained data is ensured, and the image quality of the final obtained scanned image is maintained.

16 Claims, 9 Drawing Sheets

(56)                    References Cited

U.S. PATENT DOCUMENTS

| | | | | |
|---|---|---|---|---|
| 7,283,606 | B2 * | 10/2007 | Kalender | ............. G06T 11/006 |
| | | | | 378/15 |
| 7,532,702 | B2 | 5/2009 | Hsieh | |
| 8,031,828 | B1 | 10/2011 | Deman | |
| 8,229,199 | B2 * | 7/2012 | Chen | ..................... G06T 11/006 |
| | | | | 382/128 |
| 8,509,514 | B2 * | 8/2013 | Chen | ..................... G06T 11/006 |
| | | | | 382/131 |
| 11,908,044 | B2 * | 2/2024 | Chen | ..................... G06T 11/006 |
| 2014/0231657 | A1 * | 8/2014 | Bolotnikov | .............. G01T 1/17 |
| | | | | 250/370.06 |
| 2022/0405990 | A1 * | 12/2022 | Chen | ..................... G06T 11/006 |
| 2024/0144556 | A1 * | 5/2024 | Xing | ..................... A61B 6/032 |

FOREIGN PATENT DOCUMENTS

| | | | | | |
|---|---|---|---|---|---|
| EP | 3632326 | A1 * | 4/2020 | ............ | A61B 6/032 |
| EP | 3646791 | A1 * | 5/2020 | ............ | A61B 6/545 |
| EP | 3843041 | A1 | 6/2021 | | |
| EP | 3210187 | B1 * | 8/2023 | .............. | G06T 5/77 |

* cited by examiner (a)    (b)    (c)

(d)    (e)    (f)

(g)    (h)    (i)

No measurement
data in second scan
(axial scan)

Use compensated
data of first scan
(high pitch spiral
scan)

No measurement
data in second scan
(axial scan)

Data of first scan
(a high pitch
spiral scan) after
being sampled and
rearranged Data after data
merging Use compensated
data of first scan
(high pitch spiral
scan)

(a)                    (b)                    (c)

(a)                    (b)

Filter data 1 (P$_1$) and data 2 (P$_2$), respectively, to obtain filtered data 1 (P$_1$') and filtered data 2 (P$_2$')

1301

Fit the filtered data 1 and the filtered data 2 in a reference data region

1302

Replace data corresponding to the reference data region with the fitted data to obtain compensated data 3

1303

Filter the compensated data 3 to obtain filtered data 3

1304

(a)                                      (b)

COMPUTED TOMOGRAPHY IMAGING METHOD AND APPARATUS

CROSS-REFERENCE TO RELATED APPLICATIONS

This application claims priority to Chinese Application No. 202211333377.X, filed on Oct. 28, 2022, the disclosure of which is incorporated herein by reference in its entirety.

TECHNICAL FIELD

Embodiments of the present application relate to the technical field of medical devices, and relate in particular to a computed tomography imaging method and apparatus.

BACKGROUND

Cardiovascular diseases refer to diseases that affect cardiac structure or functions, such as heart attack, stroke, heart failure, cardiac arrhythmia, and coronary artery disease (CAD). Over time, in particular as the population ages, incidences of heart disease continue to rise. Cardiovascular diseases have become the leading cause of death worldwide.

Computed tomography (CT) for the heart is generally used to acquire diagnostic information regarding cardiac or coronary artery anatomy to detect or diagnose CAD, so as to assess the patency of coronary artery bypass grafting or coronary artery stent implantation, or to assess cardiac volume and cardiac function. In developed countries, CAD is the most common cause of morbidity and death. As a non-invasive imaging technique for CAD detection, computed tomography for the heart has developed rapidly in recent years. By means of cardiac CT, physicians can acquire more diagnostic knowledge regarding cardiac structure, cardiovascular blood supply condition, myocardial dispersion related to heart attack, plaque buildup, and arteriostenosis.

The technological development of CT systems greatly improves the spatial resolution and time resolution of imaging and shortens imaging acquisition time, thereby generating high quality images of beating hearts can be achieved. After introducing 64 rows of detectors, a CT system can match a spatial resolution in a z direction with a spatial resolution in an x-y plane, so as to achieve an isotropic spatial resolution in each direction. In addition, a larger detector coverage in the z direction reduces the scanning time, and improves the time resolution of electrocardiogram-gated (ECG-gated) cardiac imaging. With the improvement of time resolution and the reduction of scanning time, ECG-gated cardiac examinations can be performed at higher heart rates. The required heart rate control and breath-holding time for a patient are also less. Therefore, cardiac CT is becoming increasingly popular for detecting and quantifying CAD and other cardiac diseases.

It should be noted that the above introduction of the background is only for the convenience of clearly and completely describing the technical solutions of the present application, and for the convenience of understanding for those skilled in the art.

SUMMARY

The inventors found that the typical length of the cardiac anatomy is about 120-140 mm. Z-direction detectors of most CT scanning devices (e.g., 64-row systems) have a length and width that are less than said length and cannot scan entire cardiac volumes within one rotation period. To cover the complete cardiac anatomy, generally, a series of slice images within several heartbeat periods are acquired. This generally results in breathing movement artifacts and registration errors of consecutively acquired images. A scanning device having a detector with a width of 160 mm in a z-axis direction can cover the entire cardiac structure within one single heartbeat period. The foregoing system which has a larger longitudinal coverage specifically designed for cardiac examinations is equipped with advanced software for scan data collection and clinical image processing, thus ensuring better image quality and more accurate cardiac disease diagnosis. However, the cost of a 256-row high-end product is much higher than that of a 64-row system, i.e., almost twice that of a 64-row system. This remains a concern for many medical institutions care about, and also increases the consumption burden for patients. When using devices having potential radiation hazards, another high-priority problem to consider is ray dose efficiency. In order to perform a cardiac examination using a CT system, the physician must choose between a smaller scanning field of view (at a low dose, but with relatively low image quality) and a full scanning field of view (with better image quality, but at a higher dose). In addition, an increase in cardiac CT utilization also means an increase in total radiation dose of the population.

With regard to at least one among the above technical problems, embodiments of the present application provide a computed tomography imaging method and apparatus in which the use of an incomplete detector reduces the total number of detecting units, reducing the cost of the scanning device; moreover, stitched data is effectively compensated, thus ensuring the quality of imaging, and reducing the radiation dose.

According to one aspect of the embodiments of the present application, a computed tomography imaging method is provided. The method includes pre-scanning an examined site by using an incomplete detector at a pitch factor of greater than 3 to obtain first data, axially scanning the examined site using the incomplete detector to obtain second data, stitching the first data and the second data to obtain third data, compensating the third data to obtain compensated third data, and performing image reconstruction by using the compensated third data to obtain a scanned image.

According to another aspect of the embodiments of the present application, a computed tomography imaging apparatus is provided. The apparatus includes a first scanning unit that pre-scans an examined site by using an incomplete detector at a pitch factor of greater than 3 to obtain first data, a second scanning unit that axially scans the examined site using the incomplete detector to obtain second data, a first processing unit that stitches the first data and the second data to obtain third data, a second processing unit that compensates the third data to obtain compensated third data, and an image reconstruction unit that performs image reconstruction by using the compensated third data to obtain a scanned image.

According to another aspect of the embodiments of the present application, an electronic device is provided which includes a memory and a processor, the memory storing a computer program, and the processor being configured to execute the computer program so as to implement the described computed tomography imaging method.

One of the benefits of the embodiments of the present application is that according to the embodiments of the present application, the use of the incomplete detector reduces the total number of detecting units, reducing the cost of the scanning device; moreover, the stitched data is effectively compensated, thus ensuring the quality of imaging, and reducing the radiation dose.

With reference to the following description and drawings, specific implementations of the embodiments of the present application are disclosed in detail, and the means by which the principles of the embodiments of the present application can be employed are illustrated. It should be understood that the implementations of the present application are therefore not limited in scope. Within the scope of the spirit and clauses of the appended claims, the implementations of the present application comprise many changes, modifications, and equivalents.

BRIEF DESCRIPTION OF THE DRAWINGS

The included drawings are used to provide further understanding of the embodiments of the present application, which constitute a part of the description and are used to illustrate the implementations of the present application and explain the principles of the present application together with textual description. Evidently, the drawings in the following description are merely some embodiments of the present application, and a person of ordinary skill in the art may obtain other implementations according to the drawings without involving inventive skill. In the drawings.

DETAILED DESCRIPTION

Figure 1:
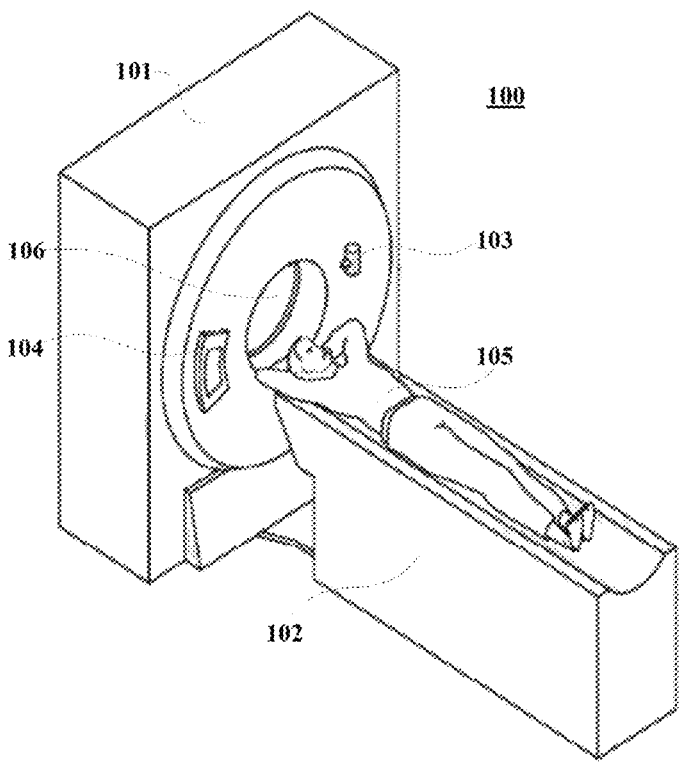
FIG. 1 is a schematic diagram of a CT imaging device according to an embodiment of the present application.

The foregoing and other features of the embodiments of the present application will become apparent from the following description and with reference to the drawings. In the description and drawings, specific implementations of the present application are disclosed in detail, and part of the implementations in which the principles of the embodiments of the present application may be employed are indicated. It should be understood that the present application is not limited to the described implementations. On the contrary, the embodiments of the present application include all modifications, variations, and equivalents which fall within the scope of the appended claims.

In the embodiments of the present application, the terms "first" and "second" etc., are used to distinguish different elements, but do not represent a spatial arrangement or temporal order, etc., of these elements, and these elements should not be limited by these terms. The term "and/or" includes any and all combinations of one or more associated listed terms. The terms "comprise", "include", "have" etc., refer to the presence of described features, elements, components, or assemblies, but do not exclude the presence or addition of one or more other features, elements, components, or assemblies.

In the embodiments of the present application, the singular forms "a" and "the", etc. include plural forms, and should be broadly construed as "a type of" or "a class of" rather than being limited to the meaning of "one". Furthermore, the term "the" should be construed as including both the singular and plural forms, unless otherwise specified in the context. In addition, the term "according to" should be construed as "at least in part according to . . . " and the term "on the basis of" should be construed as "at least in part on the basis of . . . ", unless otherwise specified in the context.

The features described and/or illustrated for one implementation may be used in one or more other implementations in the same or similar manner, be combined with features in other embodiments, or replace features in other implementations. The term "include/comprise" when used herein refers to the presence of features, integrated components, steps, or assemblies, but does not preclude the presence or addition of one or more other features, integrated components, steps, or assemblies.

The device described herein that obtains medical imaging data may be applicable to various medical imaging modalities, including but not limited to, CT (computed tomography) devices, PET (positron emission tomography)-CT, or any other suitable medical imaging devices.

The system obtaining the medical imaging data may include the aforementioned medical imaging device, and may include a separate computer device connected to the medical imaging device, and may further include a computer device connected to an Internet cloud, the computer device being connected by means of the Internet to the medical imaging device or a memory for storing medical images. The imaging method may be independently or jointly implemented by the aforementioned medical imaging device, the computer device connected to the medical imaging device, and the computer device connected to the Internet cloud.

As an example, the embodiments of the present application are described below in conjunction with an X-ray computed tomography (CT) device. Those skilled in the art will appreciate that the embodiments of the present application can also be applied to other medical imaging devices.

FIG. 1 is a schematic diagram of a CT imaging device according to an embodiment of the present application, schematically showing the situation of a CT imaging device 100. As shown in FIG. 1, the CT imaging device 100 includes a scanning gantry 101 and a patient table 102; the scanning gantry 101 has an X-ray source 103 projecting an X-ray beam towards a detector assembly or collimator 104 on an opposite side of the scanning gantry 101. A test object 105 can lie flat on the patient table 102 and be moved into a scanning gantry opening 106 along with the patient table 102. Medical imaging data of the test object 105 can be acquired by means of a scan carried out by the X-ray source 103.

Figure 2:
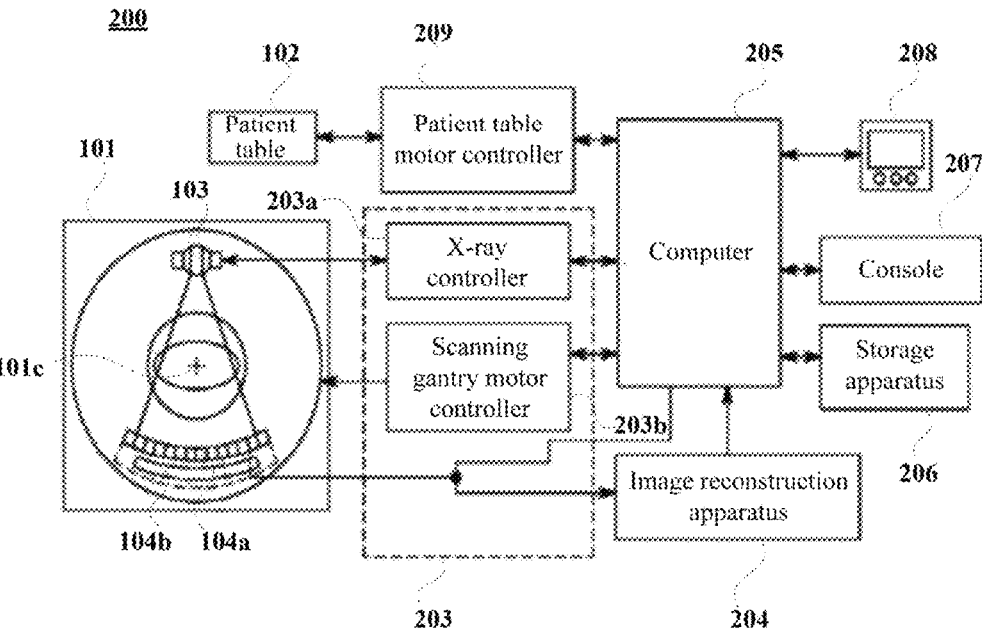
FIG. 2 is a schematic diagram of a CT imaging system according to an embodiment of the present application.

FIG. 2 is a schematic diagram of a CT imaging system according to an embodiment of the present application, schematically showing a block diagram of a CT imaging system 200. As shown in FIG. 2, the detector assembly 104 includes a plurality of detector units 104*a* and a data acquisition system (DAS) 104*b*. The plurality of detector units 104*a* sense a projected X-ray passing through the test object 105.

The DAS 104*b*, according to the sensing of the detector units 104*a*, converts collected information into projection data for subsequent processing. During the scanning for acquiring the X-ray projection data, the scanning gantry 101 and components mounted thereon rotate around a rotation center 101*c*.

The rotation of the scanning gantry 101 and the operation of the X-ray source 103 are controlled by a control mechanism 203 of the CT imaging system 200. The control mechanism 203 includes an X-ray controller 203*a* that provides power and a timing signal to the X-ray source 103 and a scanning gantry motor controller 203*b* that controls the rotational speed and position of the scanning gantry 101. An image reconstruction apparatus 204 receives the projection data from the DAS 104*b* and performs image reconstruction. A reconstructed image is transmitted as an input to a computer 205, and the computer 205 stores the image in a mass storage apparatus 206.

The computer 205 also receives commands and scanning parameters from an operator by means of a console 207. The console 207 has an operator interface of a certain form, such as a keyboard, a mouse, a voice activated controller, or any other suitable input apparatus. An associated display 208 allows the operator to observe the reconstructed image and other data from the computer 205. The commands and parameters provided by the operator are used by the computer 205 to provide control signals and information to the DAS 104*b*, the X-ray controller 203*a*, and the scanning gantry motor controller 203*b*. Additionally, the computer 205 operates a patient table motor controller 209 which controls the patient table 102 so as to position the test object 105 and the scanning gantry 101. In particular, the patient table 102 moves the test object 105 as a whole or in part to pass through the scanning gantry opening 106 in FIG. 1.

The foregoing schematically illustrates the device and the system for acquiring medical imaging data (or also referred to as medical images or medical image data) according to the embodiments of the present application, but the present application is not limited thereto. The medical imaging device may be a CT device, a PET-CT, or any other suitable imaging device. A storage device may be located within the medical imaging device, in a server outside the medical imaging device, in an independent medical imaging storage system (such as a Picture Archiving and Communication System (PACS)), and/or in a remote cloud storage system.

In addition, a medical imaging workstation may be provided locally to the medical imaging device, that is, the medical imaging workstation is provided close to the medical imaging device, and the two may both be located in a scanning room, an imaging department, or the same hospital. In contrast, a medical image cloud platform analysis system may be positioned away from the medical imaging device, for example, arranged at a cloud end that is in communication with the medical imaging device.

As an example, after a medical institution completes an imaging scan by using the medical imaging device, scan data is stored in a storage device. The medical imaging workstation may directly read the scan data and perform image processing by means of a processor thereof. As another example, the medical image cloud platform analysis system may read a medical image in the storage device by means of remote communication to provide "software as a service (SAAS)". The SAAS may exist between hospitals, between a hospital and an imaging center, or between a hospital and a third-party online diagnosis and treatment service provider.

Medical image scanning is schematically illustrated above, and the embodiments of the present application are described in detail below in view of the accompanying drawings.

Figure 3:
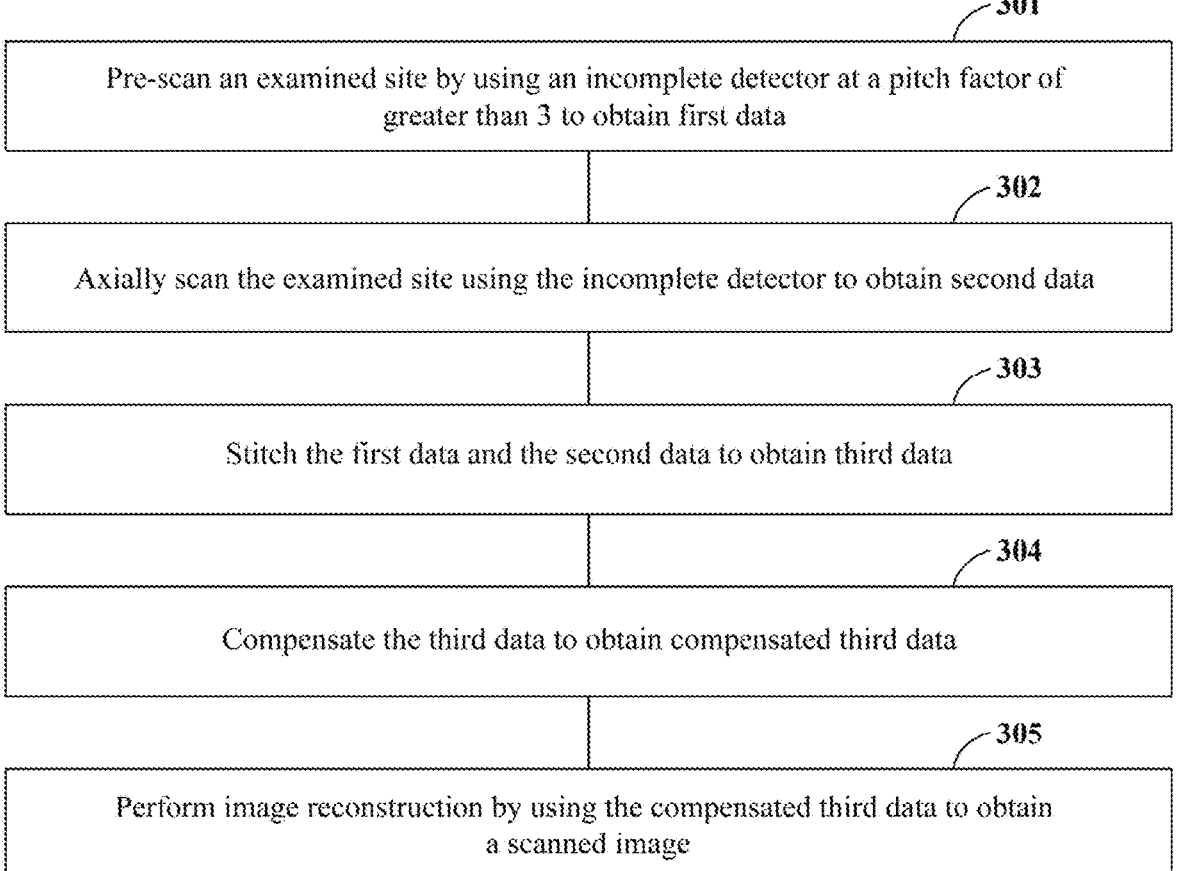
FIG. 3 is a schematic diagram of a computed tomography imaging method according to an embodiment of the present application.

Embodiments of the present application provide a computed tomography imaging method. FIG. 3 is a schematic diagram of a computed tomography imaging method according to an embodiment of the present application, and as shown in FIG. 3, the method includes 301: pre-scanning an examined site by using an incomplete detector at a pitch factor of greater than 3 to obtain first data, 302: axially scanning the examined site using the incomplete detector to obtain second data, 303: stitching the first data and the second data to obtain third data, 304: compensating the third data to obtain compensated third data, and 305: performing image reconstruction by using the compensated third data to obtain a scanned image.

It should be noted that FIG. 3 merely schematically illustrates an embodiment of the present application, but the present application is not limited thereto. For example, some other operations may also be added, or some of the operations may be omitted. Those skilled in the art can make appropriate variations according to the above content, rather than being limited by the disclosure of FIG. 3.

According to the above embodiment, by performing the two scans using the incomplete detector, the first scan (the pre-scan) obtaining an overview (first data) of patient information, and the second scan (the main scan, i.e., an axial scan) obtaining incomplete data (second data), stitching and compensating the data obtained by the two scans, and performing image reconstruction by using the compensated data, while reducing a total dose of X-rays, the integrity of the obtained data is thus ensured by the data stitching, and the image quality of the final obtained scanned image is maintained by means of the data compensation.

In the embodiment of the present application, in step 301, the examined site is pre-scanned at a high pitch (a pitch factor of greater than 3) by using the incomplete detector to obtain real scan data (the first data) of a patient, which is not used for imaging, but instead for compensating for missing data of the incomplete detector.

In the above embodiment, the incomplete detector is described relative to a complete detector. The projection image or data obtained by a complete detector is complete or, in other words, global, and the projection data or image obtained by an incomplete detector is incomplete or, in other words, local. In addition, for convenience of illustration, in the embodiments of the present application, the projection data or image that should have otherwise been obtained by the removed detector modules is referred to as missing data or a missing image.

Figure 4:
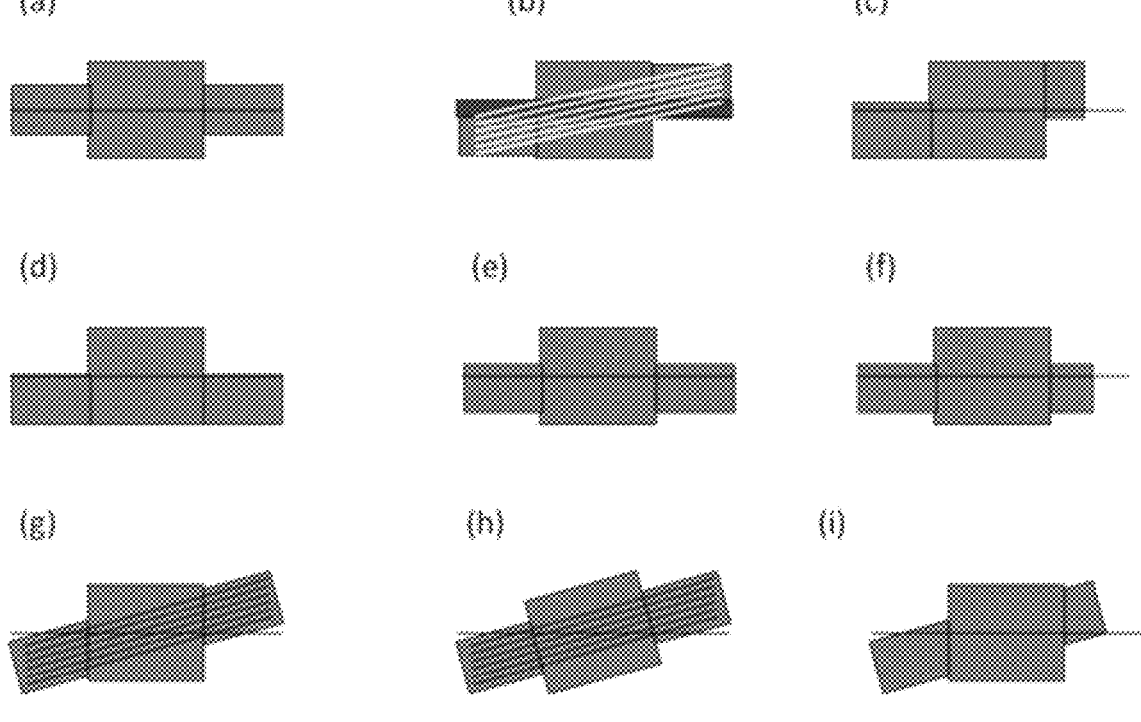
FIG. 4 is example diagrams of incomplete detectors according to embodiments of the present application.
Figure 5:
FIG. 5 is an example diagram of a complete detector according to an embodiment of the present application.

FIG. 4 is example diagrams of incomplete detectors according to embodiments of the present application, and FIG. 5 is an example diagram of a complete detector of an embodiment of the present application. As shown in FIG. 5, global projection data of a complete rectangular region may be obtained by the complete detector. As shown in FIG. 4(a), partial detector modules in four corners of a plurality of detector modules arranged in an array may be symmetrically removed, for example, half of the detector modules may be removed and half of the detector modules may be left, and the incomplete detector in FIG. 4(a) may be referred to as a cross-shaped detector. As shown in FIG. 4(b), FIG. 4(c), FIG. 4(d), FIG. 4(e), FIG. 4(f), FIG. 4(g), FIG. 4(h), and FIG. 4(i), any partial detector modules in at least one corner among four corners of a plurality of detector modules arranged in an array may also be asymmetrically removed, and local projection data of a central region may be retained in projection data of the detector. The embodiments of the present application are not limited thereto. The incomplete detector may also be a fence-shaped detector or the like, and examples will not be listed herein one by one. In the following embodiments, for convenience of illustration, the cross-shaped detector is taken as an example for illustration. Furthermore, for convenience of illustration, partial off-center detector modules removed from the plurality of detector modules arranged in an array are referred to as detector missing portions.

In the above embodiment, the pitch factor is greater than 3, for example, the pitch factor is 5, but the present application is not limited thereto, and the pitch factor may also be other values greater than 3, or may be an integer value, or may be a non-integer value, depending on the number of the detector modules, the shape of the detector, the scanning field of view (SFOV), the z-axis coverage, the image quality, and other requirements. By increasing the pitch factor at which a pre-scan is performed, the radiation dose for the patient can be reduced.

For example, in a cardiac examination, the cardiac region is the scan region of interest (i.e., the examined site), and the incomplete detector has physical detector modules disposed within a local field of view of a display field of view (DFOV), wherein the range of the physical detector modules is sufficient to cover the tissue structure of the entire heart, and the local field of view may be exemplarily selected as 25 cm or other suitable sizes. During a cardiac imaging process, data acquired by the incomplete detector in a position in which there are no physical detector modules, while contributing to final image reconstruction, contributes less to the reconstruction than data acquired by detector modules in, for example, a central position (e.g., within a 25 cm field of view corresponding to the DFOV), so the data acquired within the region does not need to have a high resolution, and can be obtained by adjusting scanning conditions (e.g., increasing the pitch). Therefore, the radiation dose can be reduced while obtaining the real data.

For example, the scanning pitch that is clinically commonly used for imaging is generally between 0.5 and 1.5. If the scanning pitch exceeds this range, it can cause severe degradation of the quality of the reconstructed image. The embodiments of the present application directly employ a pitch of greater than 3 to perform the acquisition of the first data. Taking the pitch used in ordinary chest/cardiac spiral scans being 1, whereas the pitch used in the embodiments of the present application being 3.5 as an example, increasing the pitch may reduce the scan dose by about 71%.

In the above embodiment, the examined site refers to a scan region of interest, and may be any region of an examinee (e.g., the patient), such as the head region, cardiac region, waist region, leg region, and the like. In the following embodiments, for convenience of illustration, the cardiac region is taken as an example for illustration.

In the above embodiment, the pre-scan may be implemented by a scanning mode of a spiral scan, but the present application is not limited thereto, and the scanning mode may also be any other scanning mode, such as an axial scan, a cine scan, a dual energy scan, etc., as long as comprehensive scan data can be obtained by the scan. In the following embodiments, for convenience of illustration, the spiral scan is taken as an example for illustration.

In some embodiments, the X-ray radiation dose used for the above pre-scan is less than the X-ray radiation dose used for a conventional scan. Therefore, the radiation dose for the patient can be reduced. As described previously, a reduction in the radiation dose can be achieved by increasing the pitch, and can further be achieved by reducing tube voltage and/or reducing tube current.

In some embodiments, the tube voltage used for the above pre-scan is lower than that used for a conventional scan. Therefore, the radiation dose for the patient can be further reduced. For example, a normal chest spiral scan has a tube ball voltage of 120 kV. In the embodiments of the present application, because the resolution requirement for the acquired data when acquiring the first data is not high, the tube voltage used for the scan may be less than 120 kV, for example, may be 80 kV, and thus the dose can be reduced by 55% as compared to the normal chest spiral scan.

In some embodiments, the tube current used for the above pre-scan is lower than that used for a conventional scan. Therefore, the radiation dose for the patient can be further reduced.

For example, a normal chest spiral scan has a tube ball current of 200 mA. In the embodiments of the present application, because the resolution requirement for the acquired data when acquiring the first data is not high, the tube current used for the scan may be less than 200 mA, for example, may be 40 mA, and thus the dose can be reduced by 80% as compared to the normal chest scan.

In the above embodiment, by performing the pre-scan in the spiral scanning mode by using the incomplete detector at a pitch of greater than 3, and optionally adjusting other scanning conditions, including a low tube ball voltage and/or a low tube ball current, a reduction in the overall dosage for the patient in one cardiac scan can be achieved. For example, in the embodiments of the present application, the incomplete detector is used, and the number of detector modules that acquire data is reduced by 30%-40% as compared to a traditional cardiac scan. Assuming that the scanning conditions for a conventional chest spiral scan are: pitch=1, kv=120 kv, mA=100 mA, and SFOV=50 cm, whereas in the embodiments of the present application, the scanning conditions used when obtaining the first data are: pitch=3.5, kv=80 kv, mA=20 mA, and SFOV=50 cm (no truncation in an x direction)/SFOV=25 cm (truncation in the x direction), compared to one traditional cardiac scan, the dose in one cardiac scan in the embodiments of the present application is about: 63%+(1-71%)*(1-55%)*(1-80%) =65%, that is, the dose is reduced by 35%.

By means of the pre-scan of step 301, the real scan data (the first data) of the patient can be obtained, the real scan data not being used for imaging, but instead for compensating for missing data at four corners of the cross-shaped detector. Given that the final cardiac image is within the 25 cm field of view of the DFOV, and data outside of the 25 cm field of view of the DFOV has limited influence on the image quality within the 25 cm field of view of the DFOV, the pre-scan of step 301 can thus quickly obtain rough information of the patient, and as a result of using a low dose for the scan, the total absorbed dose for the patient is reduced.

Figure 6:
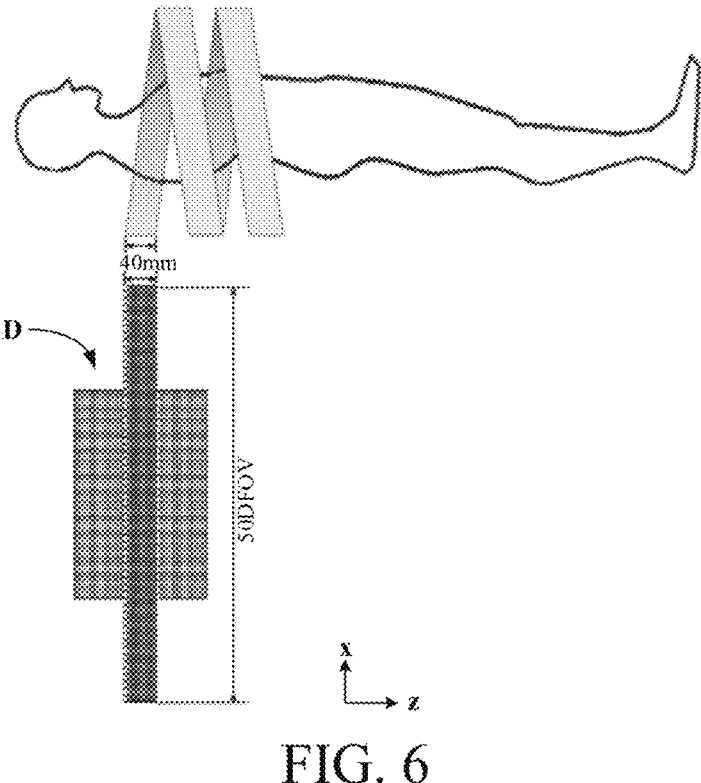
FIG. 6 is a schematic diagram of one example of a high pitch spiral scan (a pre-scan) using a cross-shaped detector.

FIG. 6 is a schematic diagram of one example of a high pitch (a pitch factor of greater than 3) spiral scan (a pre-scan) using a cross-shaped detector. As shown in FIG. 6, in the spiral scan used as the pre-scan, data is received and collected mainly using detector modules (located in the z direction, coverage of 40 mm) in a central portion in a z direction (a row direction) of the cross-shaped detector D. For the detector modules of these rows, each row of detector modules cover a full DFOV (e.g., a field of view of 50 cm), thereby covering the entire body of the patient. The scan data (referred to as the first data or data 1) obtained by the spiral scan is scan data of a full scan field of view (a full scan FOV), and is used for compensating for missing data at four corners of the cross-shaped detector and not directly used for reconstructing an image.

In the embodiment of the present application, in step 302, a typical cardiac scan is performed for cardiac CT imaging. In the above embodiment, all of the available functions and cooperative work related to the cardiac scan, such as ECG gating preparation, contrast agent injection, etc., are prepared before the scan. Thereafter, the cardiac scan may be performed in a one-rotation axial scanning mode.

For example, the cardiac scan is a single-rotation axial scan, having a rotation time of 0.23 seconds. In said axial scan, the entirety of the detector modules is used to receive X-rays passing through the patient, that is, the partial detector modules of the incomplete detector in the central portion in the x direction (a channel direction) and at both end portions in the x direction are used to collect data. The detector modules of the incomplete detector in the central portion in the x direction have a coverage in the z direction of up to 160 mm, which can cover the length range of the entire heart when scanned, and thus can collect data (the second data) of the patient's heart in one single rotation.

Figure 7:
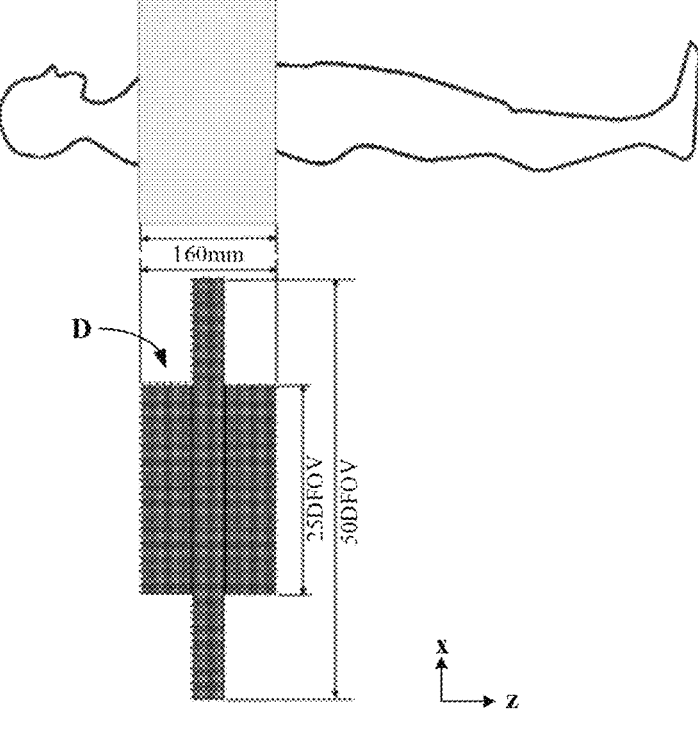
FIG. 7 is a schematic diagram of one example of a cardiac axial scan (a main scan) using the cross-shaped detector.

FIG. 7 is a schematic diagram of one example of a cardiac axial scan (a main scan) using a cross-shaped detector. As shown in FIG. 7, in this example, a one-rotation axial scanning mode is used, and in the cardiac axial scan, all detector modules of the cross-shaped detector D are used. That is, in this example, all of the detector modules of the cross-shaped detector are used to collect data (the second data) of this scan.

In the embodiment of the present application, in step 303, stitching of the first data and the second data may be performed. In the above embodiment, because the incomplete detector has an irregular shape, meaning that the detector does not have detector modules assembled in certain portions along the z axis and/or the x axis, therefore missing information for said portions is required to be filled or compensated for before image generation. In some implementations, the first data and the second data may be stitched or, in other words, the second data needs to be complemented by using the first data.

Figure 8:
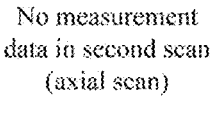
FIG. 8 is schematic diagrams for stitching or complementing data obtained by incomplete detection in a cardiac axial scan (a main scan)
Figure 8:
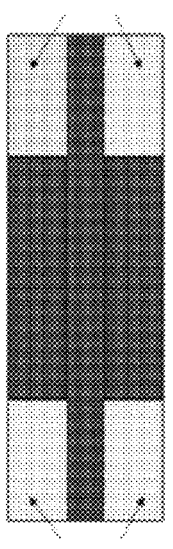
Figure 8:
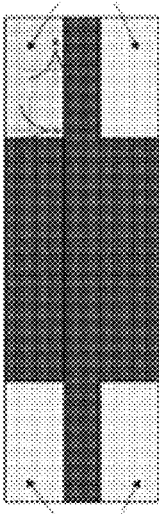

FIG. 8 is schematic diagrams for stitching or complementing data obtained by an incomplete detector in a cardiac axial scan (a main scan). As shown in FIG. 8, (a) shows the axial scan result, wherein no scan data is present at four corners of the incomplete detector; (b) shows regions missing data being filled with data obtained by the spiral scan used as the pre-scan, wherein the portions missing data in the second data obtained by the cardiac axial scan are filled by using data at four corners of the first data obtained by the spiral scan; and (c) shows data (third data) after combination of the data from two scans, wherein the data that is missing in the axial scan result is complemented by the data obtained by the spiral scan.

In some embodiments, first, the above first data may be upsampled using an interpolation algorithm, and then the upsampled first data is stitched with the second data, to obtain the third data.

In the spiral scan of the above embodiment, because of the increase in the pitch, although the speed of the scan is increased and the dose is reduced, anatomical details could be lost and artifacts could be introduced, such as windmill artifacts, sawtooth artifacts, and other artifacts, and the first data obtained directly is sparse and cannot be adequately applied to fill data in positions in the second data in which no physical detector modules are present; therefore, in the embodiment of the present application, after the first data is obtained by means of step 301, the first data is upsampled using the interpolation algorithm, and by means of the upsampling of the data, it is ensured that first data acquired by means of the high pitch spiral scan is sufficient to fill data that is missing in the second data acquired by the axial scan. At the same time, the upsampling can also effectively reduce the amount of artifacts brought about by the high pitch spiral scan, ensuring that the image quality of the final reconstructed image will not be reduced because of the high pitch.

In the above embodiment, the upsampling method may be a linear interpolation, for example, the scan data (the first data) of the spiral scan is interpolated between views, providing comprehensive complete data for analysis of image reconstruction.

In some embodiments, the equation for linear interpolation (Equation 1) is defined as:

$$p(c,v,r)=w^*p(c,v_h-1,r)+(1-w)^*p(c,v_h+1,r),v=2(v_h-1) \qquad \text{Equation 1}$$

where, $v_h$ is a ray angle index of a spiral scan, v is a corresponding ray angle index of interpolated data, c is a channel index of the spiral scan, r is a row index of the spiral scan, and w is a differential weight.

Figure 9:
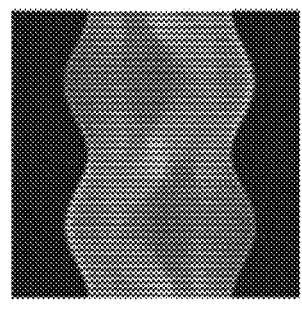
FIG. 9 is schematic diagrams of one example for upsampling data acquired by a high pitch spiral scan as a pre-scan using a linear interpolation method.
Figure 9:
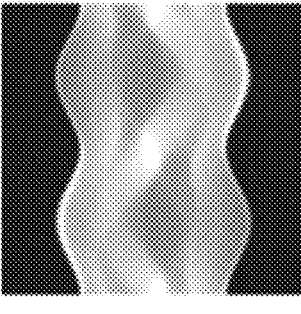

FIG. 9 is schematic diagrams of one example of upsampling data acquired by a high pitch spiral scan used as a pre-scan by using a linear interpolation method. As shown in FIG. 9, (a) shows the scan data (the first data) acquired by a high pitch spiral scan, and (b) shows upsampled data obtained after upsampling the first data by using a linear interpolation method. As can be seen from FIG. 9, relative to the sparse first data, the upsampled data obtained after interpolation is more dense, and may be used for complementing data of missing portions of the incomplete detector. In the above embodiment, after the first data is upsampled, the upsampled data may be used for compensating for missing data of the axial scan.

For each pixel in the axial scan that has no scan data, the upsampled data may be arranged into the same detector size as the axial scan and deployed to corresponding positions of four missing angles of the incomplete detector. After the data (the first data) acquired by the spiral scan used as the pre-scan is rearranged and redeployed, each row of the incomplete detector has the same number of data units, and the data (the second data) acquired by the axial scan after being compensated by means of the first data has complete data for image reconstruction.

In the foregoing embodiment, the upsampling being performed using the linear interpolation method is taken as an example, but the present application is not limited thereto, and other interpolation methods may also be used, such as a cubic interpolation method, the Lagrange interpolation method, and the like. Additionally, in addition to the interpolation method, other methods for improving data sampling rate may be employed, such as a sparse view sampling method, deep learning estimation method, and the like.

In the embodiments of the present application, because data stitching may introduce artifacts, in order to eliminate or mitigate artifacts, in step 304, in the embodiment of the present application, the third data (i.e., data after stitching the first data and the second data) is compensated prior to performing image reconstruction.

In the embodiments of the present application, the incomplete detector includes a plurality of detector modules arranged in an array. For convenience of illustration, the removed partial detector modules that are offset from the center of the incomplete detector are referred to as detector missing portions. Taking a cross-shaped detector as an example, the detector missing portions refer to missing portions of four corners of the cross-shaped detector.

In the above embodiment, the incomplete detector forms a reference data region which includes a channel of detector modules at the junction of a detector missing portion and the remaining portion of the incomplete detector (e.g., the cross portion of the cross-shaped detector) and a certain number of channels (one or more channels) of detector modules from the junction to a central position in the x direction of the incomplete detector, and a row of detector modules at the junction and a certain number of rows (one or more rows) of detector modules from the junction to a central position in the z direction of the incomplete detector, wherein each channel of the reference data region forms a reference data channel, and each row of the reference data region forms a reference data row.

In the above embodiment, if a channel of the above reference data region is selected as a reference data channel, then the reference data may refer to data acquired by detector modules of the selected channel, and if a plurality of channels of the above reference data region are selected as reference data channels, then the reference data may be one or more among an average value, a median, a maximum value and a minimum value of data acquired by detector modules of the selected plurality of channels. Similarly, if one row of the above reference data region is selected as a reference data row, then the reference data may refer to data acquired by detector modules of the selected row, and if a plurality of rows of the above reference data region are selected as reference data rows, then the reference data may be one or more among an average value, a median, a maximum value and a minimum value of data acquired by detector modules of the selected plurality of rows.

In some embodiments, compensating third data includes S1: calculating reference data of first data and second data in a reference data region, and S2: compensating data of in third data corresponding to detector missing portions by using the reference data to obtain compensated third data.

In the above embodiment, the reference data of the first data and the second data in the reference data region refers to the difference or quotient between the first data and the second data in the reference data region, i.e., the difference or quotient between the first data corresponding to the reference data region and the second data corresponding to the reference data region.

Taking a channel of the above reference data region being selected as a reference data channel as an example, first data corresponding to the reference data channel is the first data corresponding to the above channel, and similarly, second data corresponding to the reference data channel is the second data corresponding to the above channel.

Taking a plurality of channels of the reference data region described above being selected as reference data channels as an example, first data corresponding to the reference data channels is one or more among an average value, a median, a maximum value and a minimum value of the first data corresponding to the plurality of channels, and similarly, second data corresponding to the reference data channels is one or more among an average value, a median, a maximum value and a minimum value of the second data corresponding to the plurality of channels.

In the above embodiment, in S1, optionally, the first data and the second data may also be filtered, and reference data of the filtered first data and second data in the reference data region is calculated.

For example, the first data and the second data are filtered in a channel direction (the x direction) of the incomplete detector, to obtain channel-direction filtered first data and second data, and reference data of the channel-direction filtered first data and second data at a reference data channel in the channel direction is calculated.

In another example, the first data and the second data are filtered in a channel direction (the x direction) and a row direction (the z direction) of the incomplete detector, respectively, to obtain channel-direction filtered first data and second data and row-direction filtered first data and second data; reference data of the channel-direction filtered first data and second data at the reference data channel in the channel direction, and reference data of the row-direction filtered first data and second data at the reference data row in the row direction are calculated; and the reference data at the reference data channel in the channel direction and the reference data at the reference data row in the row direction are used to obtain the reference data of the first data and the second data in the reference data region.

In the above embodiment, in S2, compensating the data in the third data corresponding to the detector missing portions by using the reference data can be adding or multiplying the third data with the reference data, to obtain the compensated third data.

For example, if the reference data of the first data and the second data in the reference data region is the difference between the first data and the second data in the reference data region, then the third data can be added with the reference data as the compensated third data, and if the reference data of the first data and the second data in the reference data region is a quotient between the first data and the second data in the reference data region, then the third data may be multiplied with the reference data as the compensated third data.

In the above embodiment, optionally, the compensated third data may also be filtered, and the filtered data may be used as the compensated third data.

For example, the added or multiplied data is filtered to obtain filtered data as the compensated third data. In another example, the added or multiplied data is subjected to filtering in the channel direction and in the row direction, respectively, to obtain filtered data as the compensated third data.

In the above embodiment, the filtering method is not restricted, and the filtering method may be mean filtering, Gaussian filtering, median filtering, Wiener filtering, and the like.

In some other embodiments, compensating third data includes S1': fitting first data and the second data in a reference data region to obtain fitted data, and S2': compensating data in third data corresponding to detector missing portions by using the fitted data to obtain compensated third data.

In the above embodiment, in S1', optionally, the first data and the second data may also be filtered, and the filtered first data and second data are fitted in the reference data region to obtain the fitted data.

For example, the first data and the second data are filtered in the channel direction of the incomplete detector to obtain channel-direction filtered first data and second data, and the channel-direction filtered first data and second data are fitted at the reference data channel in the channel direction to obtain the fitted data.

In the above embodiment, in S2', compensating data in the third data corresponding to the detector missing portions by using the fitted data can be replacing the third data of the reference data region with the fitted data to obtain replaced data as the compensated third data.

region of the cross-shaped detector in which there are detector missing portions, positions of a first row and last row thereof are represented by $-r_0$ and $r_0$, respectively, while with regard to a region of the cross-shaped detector in which there are no detector missing portions (a region having the largest scan range in the z direction), positions of a first row and last row thereof are represented by $-r_f$ and $r_f$, respectively. In addition, when the data 1 and the data 2 are stitched, the width of the reference data region in the detector channel direction (the x direction) is represented by d, where d may be less than 0 or greater than 0, that is, the reference data channel may be a data channel at the junction, or may be several data channels from the junction to the center in the x direction of the cross-shaped detector.

In this example, the data 1 and the data 2 are stitched to obtain the data 3, that is, in the portions (missing portions of four corners) in which there are no detector modules of the cross-shaped detector, the data 3 is filled with the data 1, and in the portion in which there are detector modules (the cross-shaped portion) of the cross-shaped detector, the data 3 is filled with the data 2. The foregoing can be expressed by the following equation (Equation 2):

$$P_s(c, r) = \begin{cases} P_s(c, r), & c_0 \le c \le c_f \text{ and } -r_f \le r \le -r_a, -c_f \le c \le -c_a \text{ and } -r_f \le r \le -r_0, c_0 \le c \le c_f \text{ and } r_0 \le r \le r_f, -c_f \le c \le -c_0 \text{ and } r_0 \le r \le r_f \\ P_s, & \text{otherwise} \end{cases}$$

<div style="text-align:right">Equation 2</div>

In the above embodiment, optionally, the compensated third data may also be filtered. For example, the replaced data is filtered to obtain filtered data as the compensated third data.

The data stitching and data compensation according to the embodiments of the present application are described below with reference to a specific example. In this example, the cross-shaped detector is still used as an example. The first data obtained in step 301 is referred to as data 1, and is represented by $P_1$, the second data obtained in step 302 is referred to as data 2, and is represented by $P_2$, and the third data obtained in step 303 (i.e., the data obtained after stitching the first data and the second data) is referred to as data 3, and is represented by $P_3$. In the embodiments of the present application, it is required to compensate the data 3. In addition, in this example, c is used to represent the position of a cth detector module in the detector channel direction (the x direction), r is used to represent the position of a rth detector module in the detector row direction (the z direction), and $P_3$ (c, r) is used to represent corresponding data of data 3 on the detector module.

Figure 10:
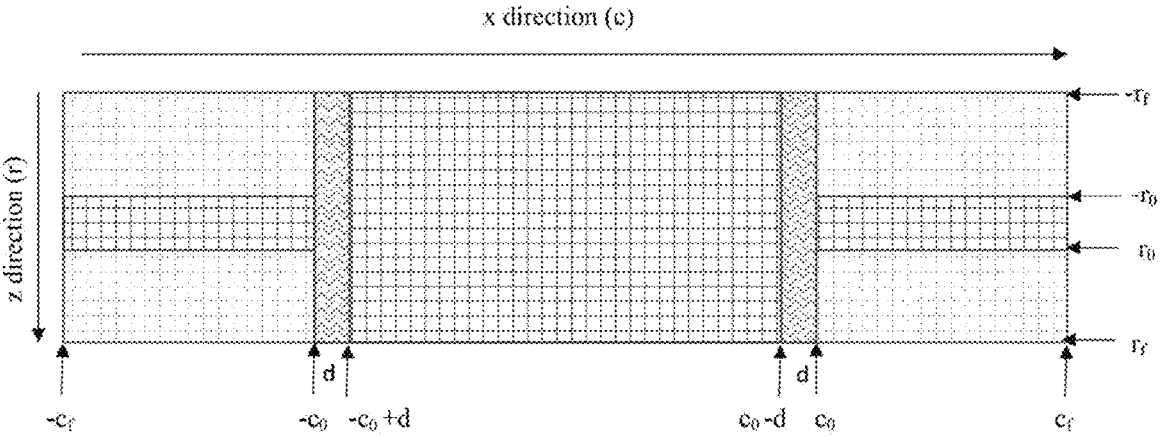
FIG. 10 is a schematic diagram of the cross-shaped detector.

FIG. 10 is a schematic diagram of the cross-shaped detector. As shown in FIG. 10, in the x direction, with regard to a region of the cross-shaped detector in which there are detector missing portions, positions of a first detector module and last detector module thereof are represented by $-c_0$ and $c_0$, respectively, while with regard to a region of the cross-shaped detector in which there are no detector missing portions (a full scan region), positions of a first detector module and last detector module thereof are represented by That is, in regions in which $c_0 \le c \le c_f$ and $-r_f \le r \le -r_0$, $-c_f \le c \le -c_0$ and $-r_f \le r \le -r_0$, $c_0 \le c \le c_f$ and $r_0 \le r \le$, or $r_f$, $-c_f \le c \le -c_0$ and $r_0 \le r \le r_f$, $P_3(c, r) = P_1(c, r)$; and in the remaining region, $P_3$ (c, r)=$P_2$(c, r).

Figure 11:
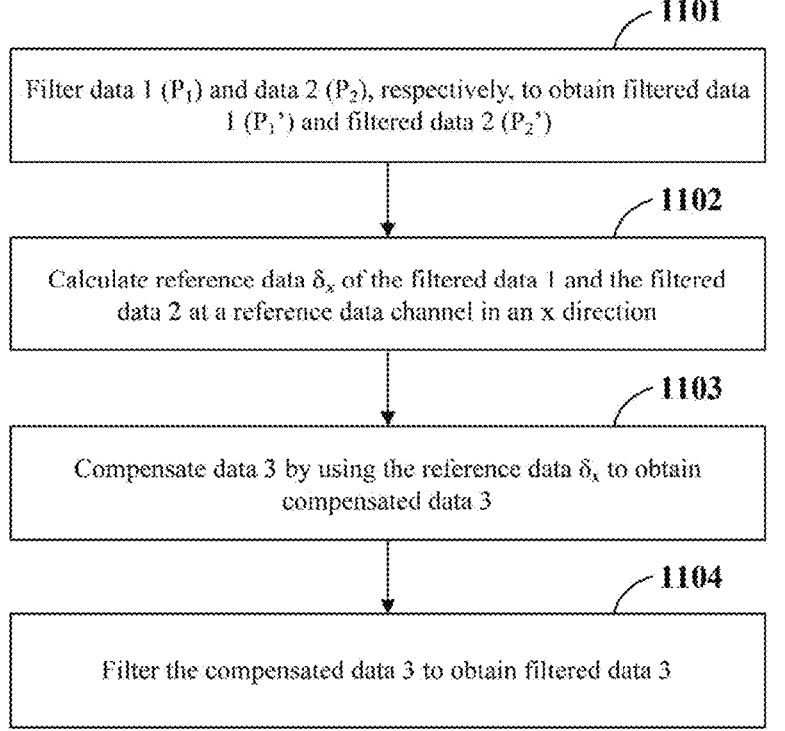
FIG. 11 is a schematic diagram for data compensation of data 3.

In this example, compensating the data 3 may be implemented by means of the method of FIG. 11. As shown in FIG. 11, the method includes 1101: filtering data 1 ($P_1$) and data 2 ($P_2$), respectively, to obtain filtered data 1 ($P_1'$) and filtered data 2 ($P_2'$), 1102: calculating reference data $\delta_x$ of the filtered data 1 and the filtered data 2 at the reference data channel in the x direction, 1103: compensating data 3 with the reference data $\delta_x$ to obtain compensated data 3, and 1104: filtering the compensated data 3 to obtain filtered data 3.

In the example of FIG. 11, for each row of detector modules of the regions of the cross-shaped detector in which there are detector missing portions, data in the data 3 corresponding to the detector missing portions is compensated by using the reference data of the reference data region.

For example, for the missing data on one side of the rth row of detector modules, first, the data 1 and the data 2 are filtered in the x direction (the filter is $H_x$), respectively, the filtering method including but not limited to mean filtering, Gaussian filtering, median filtering, Wiener filtering, and the like. Data $P_1'$ and $P_2'$ are obtained, see Equation 3.

$$P_1'(c,r)=H_{x1}(c)*P_1(c,r), P_2'(c,r)=H_{x2}(c)*P_2(c,r) \qquad \text{Equation 3}$$

Thereafter, subtraction is performed between data at the $c_0$–dth channel of $P_1'$ and data at the $c_0$–dth channel of $P_2'$, thereby obtaining reference data $\delta_x$ of the data 1 and the data 2 at the reference data channel, see Equation 4.

$$\delta_x(c, r) = \begin{cases} P_1'(c_0 - d, r) - P_2'(c_0 - d, r), & c_0 - d \le c \le c_f \text{ and } r_0 \le r \le r_f, c_0 - d \le c \le c_f \text{ and } -r_f \le r \le -r_0 \\ P_1'(-c_0 + d, r) - P_2'(-c_0 + d, r), & -c_f \le c \le -c_0 + d \text{ and } r_0 \le r \le r_f, -c_f \le c \le -c_0 + d \text{ and } -r_f \le r \le -r_0 \\ 0, & \text{otherwise} \end{cases}$$

<div style="text-align:right">Equation 4</div>

$-c_f$ and $c_f$, respectively. In the z direction, with regard to a

That is, in regions in which $c_0-d\leq c\leq c_f$ and $r_0\leq r\leq r_f$ or $c_0-d\leq c\leq c_f$ and $-r_f\leq r\leq-r_0$, $\delta_x(c,r)=P_1'(c_0-d,r)-P_2'(c_0-d,r)$; in regions in which $-c_f\leq c\leq-c_0+d$ and $r_0\leq r\leq r_f$ or $-c_f\leq c\leq-c_0+d$ and $-r_f\leq r\leq-r_0$, $\delta_x(c,r)=P_1'(-c_0+d,r)-P_2'(-c_0-d,r)$; and in the remaining region, $\delta_x(c, r)=0$.

Thereafter, for the rth row of detectors of the stitched data 3 ($P_3$), data between channel $c_0-d$ and $c_f$ is amended (compensated) by using $\delta_x$, see Equation 5.

$$P_3'(c,r)=P_3(c,r)+\delta_x(c,r) \qquad \text{Equation 5}$$

For other data corresponding to the detector missing portions, a similar method is used to carry out amendments (compensate).

In the foregoing example, the reference data being the difference between the first data and the second data at the reference data channel is taken as an example. In other examples, the reference data may also be a quotient between the first data and the second data at the reference data channel. Then, in these examples, division is performed between data of the $c_0-d$th channel of $P_1'$ and data of the $c_0-d$th channel of $P_2'$ to obtain the reference data $\delta_x$ of the data 1 and the data 2 at the reference data channel, see Equation 6.

$$\delta_x(c,r)=\begin{cases} P_1'(c_0-d,r)/P_2'(c_0-d,r), & c_0-d\leq c\leq c_f \text{ and } r_0\leq r\leq r_f, c_0-d\leq c\leq c_f \text{ and } -r_f\leq r\leq-r_0 \\ P_1'(-c_0+d,r)/P_2'(-c_0+d,r), & -c_f\leq c\leq-c_0+d \text{ and } r_0\leq r\leq r_f, -c_f\leq c\leq-c_0+d \text{ and } -r_f\leq r\leq-r_0 \\ 1, & \text{otherwise} \end{cases} \qquad \text{Equation 6}$$

That is, in regions in which $c_0-d\leq c\leq c_f$ and $r_0\leq r\leq r_f$ or $c_0-d\leq c\leq c_f$ and $-r_f\leq r\leq-r_0$, $\delta_x(c,r)=P_1'(c_0-d,r)-P_2'(c_0-d,r)$; in regions in which $-c_f\leq c\leq-c_0+d$ and $r_0\leq r\leq r_f$ or $-c_f\leq c\leq-c_0+d$ and $-r_f\leq r\leq-r_0$, $\delta_x(c,r)=P_1'(-c_0+d,r)-P_2'(-c_0-d,r)$; and in the remaining region, $\delta_x(c, r)=1$.

In this example, for the rth row of detectors of the stitched data 3 ($P_3$), data between channel $c_0-d$ and $c_f$ is amended by using $\delta_x$, see Equation 7.

$$P_3'(c,r)=P_3(c,r)*\delta_x(c,r) \qquad \text{Equation 7}$$

In the above example, after the compensated data 3 is obtained, the compensated data 3 may also be filtered in the x direction, the filtering method including but not limited to mean filtering, Gaussian filtering, median filtering, Wiener filtering, and the like.

For example, for each row of detector modules of the regions of the cross-shaped detector in which there are detector missing portions, filtering is performed to obtain the filtered data 3 as a compensation result, see Equation 8.

$$P_3''=H_3*P_3'(C,R) \qquad \text{Equation 8}$$

In the above example, the data 1 and the data 2, and the compensated data 3 being filtered is taken as an example, but the present application is not limited thereto, and the data 1 and the data 2 and the compensated data 3 may also not be filtered, but instead the above reference data can be calculated directly from the data 1 and the data 2, or the compensated data 3 can be directly used as the compensation result.

Figure 12:
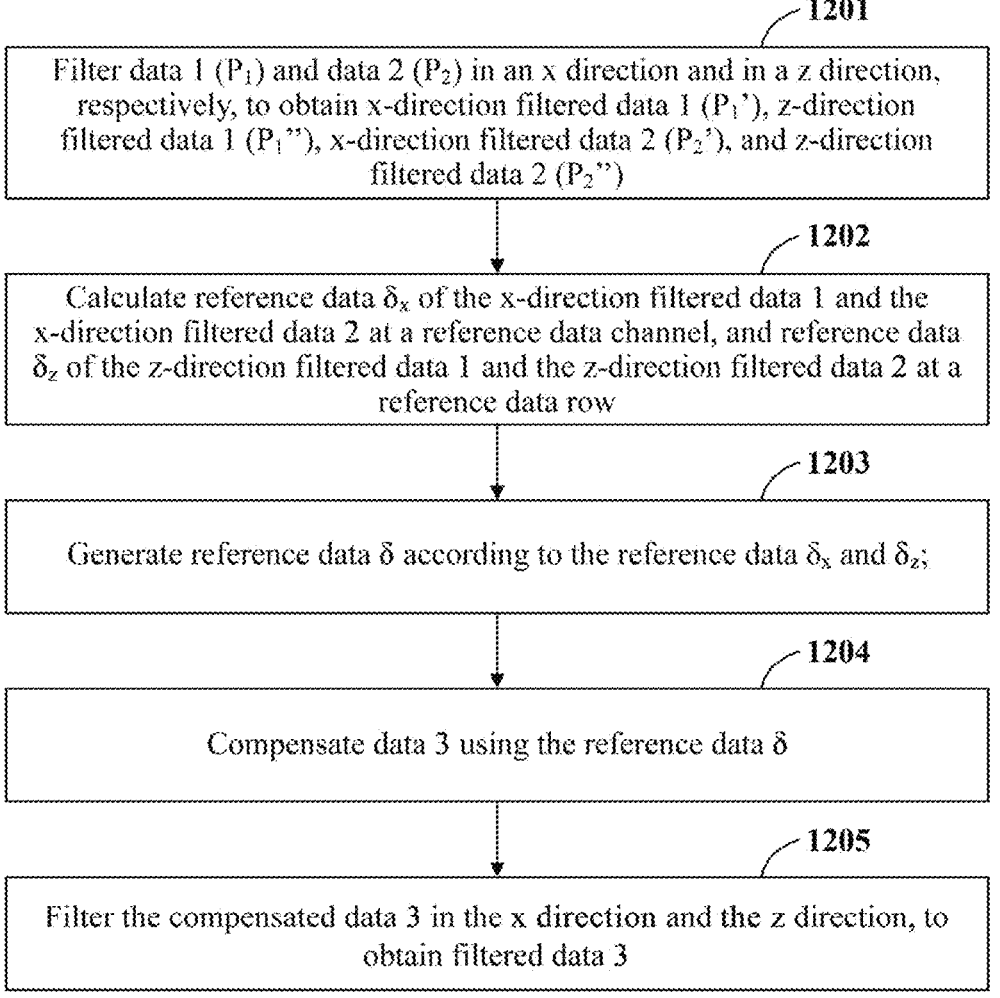
FIG. 12 is another schematic diagram for data compensation of the data 3.

In this example, compensating the data 3 may also be implemented by the method of FIG. 12. As shown in FIG. 12, the method includes 1201: filtering data 1 ($P_1$) and data 2 ($P_2$) in an x direction and in a z direction, respectively, to obtain x-direction filtered data 1 ($P_1'$), z-direction filtered data 1 ($P_1''$), x-direction filtered data 2 ($P_2'$), and z-direction filtered data 2 ($P_2''$), 1202: calculating reference data $\delta_x$ of the x-direction filtered data 1 and the x-direction filtered data 2 at a reference data channel, and reference data $\delta_z$ of the z-direction filtered data 1 and the z-direction filtered data 2 at a reference data row, 1203: generating reference data $\delta$ according to the reference data $\delta_x$ and $\delta_z$, 1204: compensating data 3 using the reference data $\delta$, and 1205: filtering the compensated data 3 in the x direction and the z direction, to obtain filtered data 3.

In the example of FIG. 12, for each row of detector modules of the regions of the cross-shaped detector in which there are detector missing portions, data in the data 3 corresponding to the detector missing portions is also compensated by using the reference data of the reference data region. Unlike the example of FIG. 11, in the example of FIG. 12, data compensation processing is performed not only in a channel direction (the x direction) of the cross-shaped detector, but also in a row direction (the z direction) of the cross-shaped detector.

For example, with regard to the missing data on one side of the rth row of detector modules, first, the data 1 and the data 2 are filtered in the x direction (the filter is $H_x$), the filtering method including but not limited to mean filtering, Gaussian filtering, median filtering, Wiener filtering, and the like, to obtain data $P_1'$ and $P_2'$, see Equation 3; then, subtraction or division is performed between data of the $c_0-d$th channel of $P_1'$ and data of the $c_0-d$th channel of $P_2'$, see Equation 4 and Equation 6, thereby obtaining the difference or quotient $\delta_x$ between the filtered data 1 and the filtered data 2 at a reference data channel in the x direction.

Similarly, with regard to the missing data on one side of the cth detector channel, first, the data 1 and the data 2 are filtered in the z direction (the filter is $H_z$), the filtering method including but not limited to mean filtering, Gaussian filtering, median filtering, Wiener filtering, and the like, to obtain data $P_1''$ and $P_2''$, see Equation 9. Then, subtraction (see Equation 10) or division (see Equation 11) is performed between data of the $r_0$th row of $P_1''$ and data of the $r_0$th row of $P_2''$, thereby obtaining the difference or quotient $\delta_z$ between the filtered data 1 and the filtered data 2 at a reference data row in the z direction.

$$P_1''(c,r)=H_{z1}(r)*P_1(c,r),P_2''(c,r)=H_{z2}(r)*P_2(c,r) \qquad \text{Equation 9}$$

$$\delta_s(c,r)=\begin{cases} P_1''(c,r_0)-P_2''(c,r_0), & c_0-d\leq c\leq c_f \text{ and } r_0\leq r\leq r_f, -c_f\leq c\leq-c_0 \text{ and } r_0\leq r\leq r_f \\ P_1''(c,r_0)-P_2''(c,r_0), & c_0-d\leq c\leq c_f \text{ and } -r_f\leq r\leq-r_0, -c_f\leq c\leq-c_0+d \text{ and } -r_f\leq r\leq-r_0 \\ 0, & \text{otherwise} \end{cases} \qquad \text{Equation 10}$$

-continued $$\delta_s(c, r) = \begin{cases} P_1''(c, r_0)/P_2''(c, r_0), c_0 - d \le c \le c_f \text{ and } r_0 \le r \le r_f, -c_f \le c \le -c_0 \text{ and } r_0 \le r \le r_f \\ P_1''(c, r_0)/P_2''(c, r_0), , c_0 - d \le c \le c_f \text{ and } -r_f \le r \le -r_0, -c_f \le c \le -c_0 + d \text{ and } -r_f \le r \le -r_0 \\ 0, \text{ otherwise} \end{cases}$$  Equation 11

Thereafter, $\delta_x$ and $\delta_z$ are combined to obtain $\delta$, see Equation 12.

$$\delta(c,r) = \text{curve}(\delta_x(c,r), \delta_z(c,r))$$  Equation 12

The above Equation 12 gives an example for generating reference data $\delta$ according to reference data $\delta_x$ and $\delta_z$, but the present application is not limited thereto, and other equations may also be used as necessary to generate the reference data, for example, a weighting method or a curve fitting method may be used to obtain the reference data $\delta$ according to the reference data $\delta_x$ and $\delta_z$.

In the above example, after the reference data $\delta$ is obtained, data of the rth row of detector modules of the stitched data 3 located that is between channels $r_0$ and $r_f$ can be amended (compensated) by using the reference data $\delta$, see Equations 13 and 14. For other data corresponding to the detector missing portions, a similar method is used to perform amendments (compensate).

$$P_3'(c,r) = P_3(c,r) + \delta(c,r)$$  Equation 13

$$P_3'(c,r) = P_3(c,r) * \delta(c,r)$$  Equation 14

$$P_3'(c, r) = \begin{cases} f(P_3'(c_0, r), P_2'(c_0 - d, r)), c_0 - d \le c \le c_f \text{ and } r_0 \le r \le r_f, -c_0 \le c \le -c_0 \text{ and } r_0 \le r \le r_f \\ f(P_1'(-c_0, r), P_2'(-c_0 + d, r)), c_0 \le c \le c_0 \text{ and } -r_f \le r \le -r_0, -c_0 \le c \le -c_0 + d \text{ and } -r_f \le r \le -r_0 \\ P_3, \text{ otherwise} \end{cases}$$  Equation 15

In the above example, the compensated data 3 may also be filtered, the filtering method including but not limited to mean filtering, Gaussian filtering, median filtering, Wiener filtering, and the like. For example, for each row of detector modules of the regions of the cross-shaped detector in which there are detector missing portions, filtering in the x direction and filtering in the z direction are performed to obtain the filtered data 3 as a compensation result.

In the above example, the data 1 and the data 2, and the compensated data 3 being filtered in the x direction and in the z direction is taken as an example, but the present application is not limited thereto, and the data 1 and the data 2 and the compensated data 3 may also not be filtered in the x direction and in the z direction, but instead the above reference data can be calculated directly from the data 1 and the data 2, or the compensated data 3 can be directly used as the compensation result.

Figure 13:
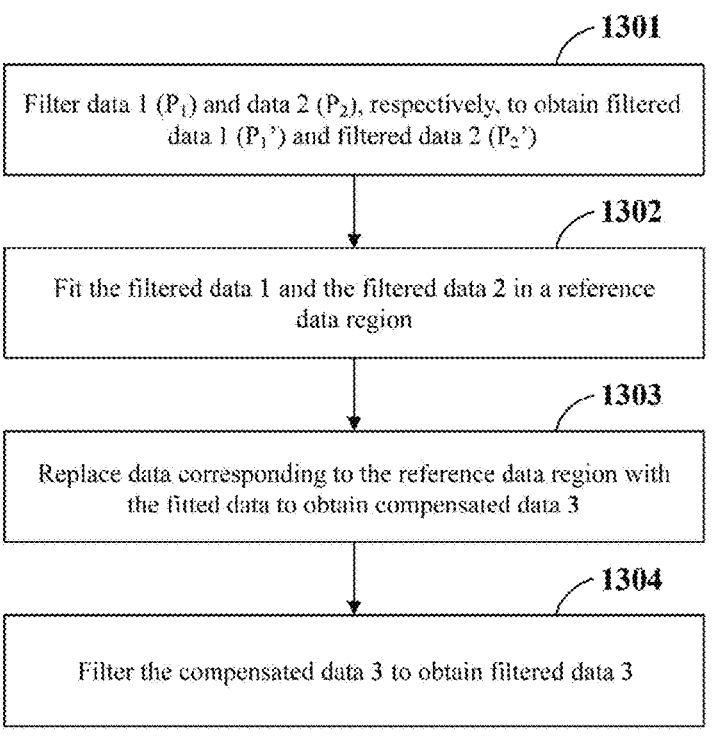
FIG. 13 is yet another schematic diagram for data compensation of the data 3.

In this example, compensating the data 3 may also be implemented by means of the method of FIG. 13. As shown in FIG. 13, the method includes 1301: filtering data 1 ($P_1$) and data 2 ($P_2$), respectively, to obtain filtered data 1 ($P_1'$) and filtered data 2 ($P_2'$), 1302: fitting the filtered data 1 and the filtered data 2 in a reference data region, 1303: replacing data corresponding to the reference data region with the fitted data to obtain compensated data 3, and 1304: filtering the compensated data 3 to obtain filtered data 3.

In the example of FIG. 13, for each row of detector modules of the regions of the cross-shaped detector in which there are detector missing portions, data in the data 3 corresponding to the detector missing portions is also compensated by using the reference data of the reference data region. Unlike the examples of FIGS. 11 and 12, in the example of FIG. 13, the reference data of the reference data region is obtained by fitting the data 1 and the data 2 of the reference data region.

For example, for the missing data on one side of the rth row of detector modules, first, the data 1 and the data 2 are filtered in the x direction, the filtering method including but not limited to mean filtering, Gaussian filtering, median filtering, Wiener filtering, and the like, to obtain data $P_1'$ and $P_2'$, see Equation 3; then, data of the $c_0$th channel of $P_1'$ is selected as a starting point and data of the$c_0$-dth channel of $P_2'$ is selected as an ending point, estimated data of other detector channel positions between the starting point and the ending point is calculated by using a function curve relationship f between the two points, and unknown data at corresponding detector channels in the data 3 is replaced with the calculated estimated data, to obtain the compensated data 3 ($P_3'$), see Equation 15. For other data corresponding to the detector missing portions, a similar method is used to make amendments (compensate).

In the above example, the compensated data 3 may also be filtered, the filtering method including but not limited to mean filtering, Gaussian filtering, median filtering, Wiener filtering, and the like. For example, for each row of detector modules of the regions of the cross-shaped detector in which there are detector missing portions, filtering is performed to obtain the filtered data 3 as a compensation result.

In the above example, the data 1 and the data 2, and the compensated data 3 being filtered is taken as an example, but the present application is not limited thereto, and the data 1 and the data 2 and the compensated data 3 may also not be filtered, but instead the above reference data can calculated directly from the data 1 and the data 2, or the compensated data 3 can be directly used as the compensation result.

In the foregoing example, the data 1 and the data 2 may be data before pre-processing. If the data 1 and the data 2 are stitched before being pre-processed to generate the data 3 and the stitched data is compensated, then after the compensation of this step, the compensated data 3 (the filtered data 3) may also be pre-processed, and the processed data 3 is used for image reconstruction.

In the foregoing example, the data 1 and the data 2 may also be data after pre-processing. If the data 1 and the data 2 are stitched after being pre-processed to generate the data 3 and the stitched data is compensated, then after the compensation of this step, the compensated data 3 (the filtered data 3) need not be pre-processed, and the data 3 can be directly used for image reconstruction.

In the embodiment of the present application, in step 305, the image reconstruction may be performed using the compensated third data.

Still using the CT scan of the heart as an example, the spiral scan data (the first data, the obtained data is complete because a scanned object or target scanned tissue is comprehensively scanned in the pre-scan, but the obtained data is relatively sparse because the pre-scan is a spiral scan having a high pitch) of the cardiac region is obtained by means of the pre-scan of step 301; the axial scan data (the second data, the data obtained by means of the scan of step 302 is local because the incomplete detector is used) of the cardiac region is obtained by means of the scan of step 302; the first data and the second data are stitched to obtain the third data of the cardiac region (the second data is complemented by using the first data to obtain complete data); the third data is compensated by using reference data to obtain the compensated third data (after compensation, artifacts that may be present during stitching are eliminated or weakened, enabling the imaging quality to be better); and the compensated third data is used for imaging of a cardiac image.

In the above example, the specific image reconstruction method is not restricted, and any method for image reconstruction (generation) may be used. In addition, other image post-processing techniques may be used, such as image filtering, noise reduction, phase selection, image fusion, and the like. For example, a filtered back projection (FBP) method, an adaptive statistical iterative reconstruction (ASiR-V) method and the like may be used to reduce the noise level.

In the above example, a generated 2D cross-sectional cardiac image may also be used to generate a 3D multi-plane recombined image and a CT angiography (CTA) image of the patient's heart, and the scope and the field of the application thereof are not limited in the present application.

Figure 14:
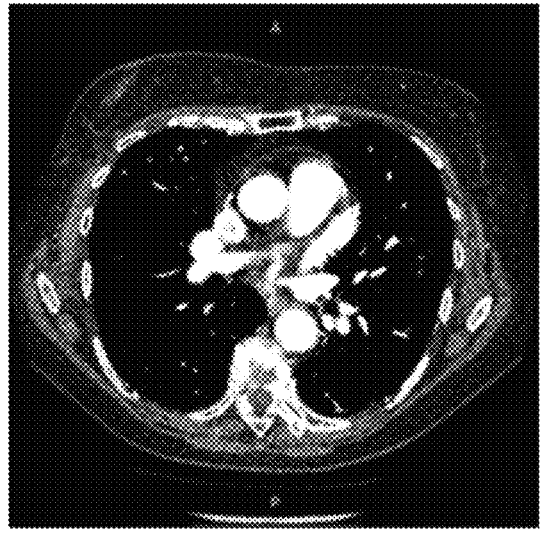
FIG. 14 is schematic diagrams of a cardiac image generated using a traditional CT imaging method and a cardiac image generated using a CT imaging method according to an embodiment of the present application.
Figure 14:
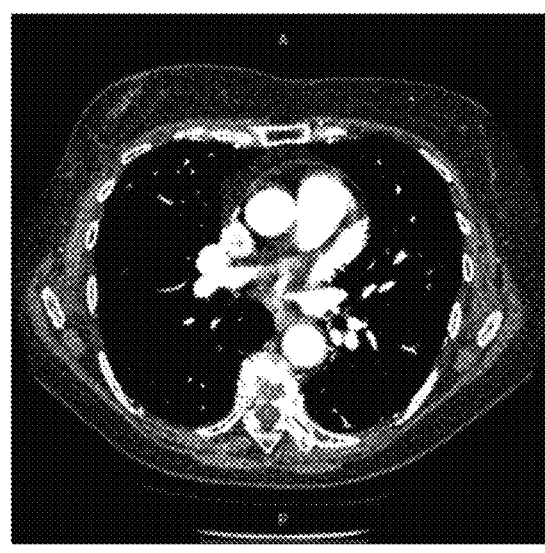

FIG. 14 is schematic diagrams of a cardiac image generated using a traditional CT imaging method and a cardiac image generated using a CT imaging method according to an embodiment of the present application. As shown in FIG. 14, (a) shows a cardiac image generated using the traditional CT imaging method, and (b) shows a cardiac image generated using the CT imaging method according to an embodiment of the present application. As can be seen from FIG. 14, by comparison, the image quality of the cardiac image generated by the CT imaging method according to the embodiment of the present application is the same as that of the cardiac image generated by the traditional CT imaging method, and there is no significant difference observed. However, by using the CT imaging method according to the embodiment of the present application, the total dose for the patient undergoing the cardiac scan is reduced, thus the radiation damage to the human body is reduced.

The above embodiments merely provide illustrative descriptions of the embodiments of the present application. However, the present application is not limited thereto, and appropriate variations may be made on the basis of the above embodiments. For example, each of the above embodiments may be used independently, or one or more among the above embodiments may be combined.

According to the embodiments of the present application, by performing the two scans using the incomplete detector, and stitching and compensating the data obtained by the two scans, while reducing the total dose of X-rays, the integrity of the obtained data is ensured, and the image quality of the final obtained scanned image is maintained.

Embodiments of the present application provide a computed tomography imaging apparatus, and content identical to that of the embodiments of the first aspect is not repeated herein.

Figure 15:
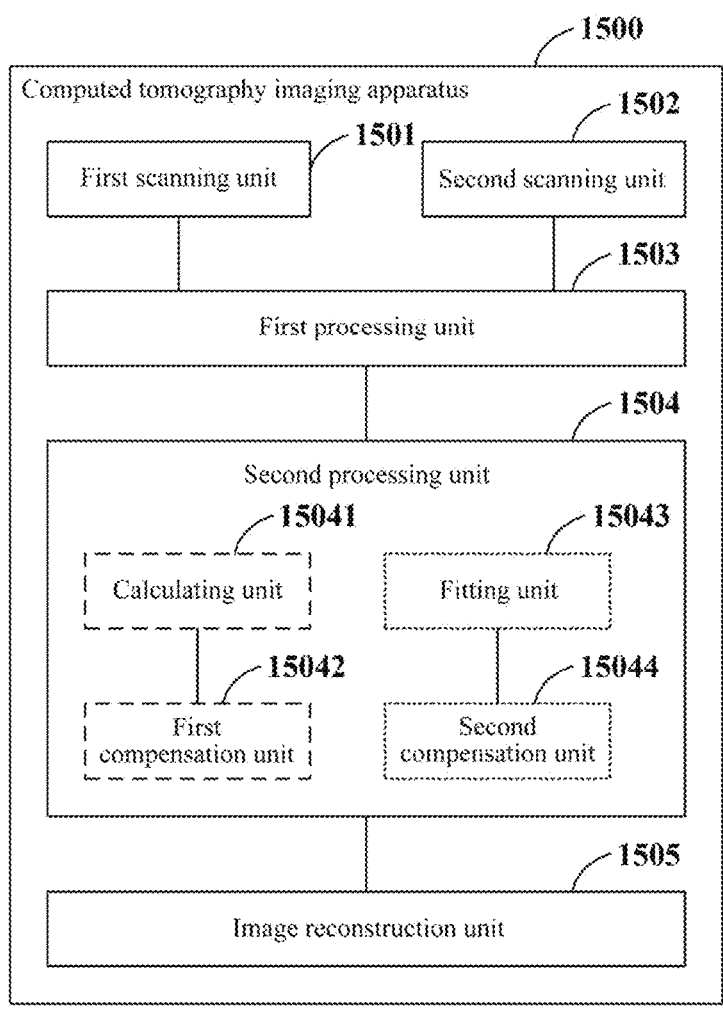
FIG. 15 is a schematic diagram of a computed tomography imaging apparatus according to an embodiment of the present application.

FIG. 15 is a schematic diagram of a computed tomography imaging apparatus according to an embodiment of the present application. As shown in FIG. 15, the computed tomography imaging apparatus 1500 includes a first scanning unit 1501 that pre-scans an examined site by using an incomplete detector at a pitch factor of greater than 3 to obtain first data, a second scanning unit 1502 that axially scans the examined site using the above incomplete detector to obtain second data, a first processing unit 1503 that stitches the above first data and the above second data to obtain third data, a second processing unit 1504 that compensates the above third data to obtain compensated third data, and an image reconstruction unit 1505 that performs image reconstruction by using the above compensated third data to obtain a scanned image.

In some embodiments, a tube voltage used for the above pre-scan is lower than that used for a conventional scan, and/or a tube current used for the above pre-scan is lower than that used for a conventional scan. In some embodiments, the X-ray radiation dose used for the above pre-scan is less than the X-ray radiation dose used for a conventional scan.

In some embodiments, the first processing unit 1503 stitching the first data and the second data includes: upsampling the first data using an interpolation algorithm; and stitching the upsampled first data with the second data to obtain the third data.

In some embodiments, the incomplete detector includes detector missing portions partial off-center detector modules of which are removed from a plurality of detector modules arranged in an array.

In some embodiments, as shown in FIG. 15, the second processing unit 1504 includes a calculating unit 15041 that calculates reference data of the first data and the second data in a reference data region, and a first compensation unit 15042 that compensates data in the third data corresponding to the detector missing portions by using the reference data to obtain the compensated third data.

In some embodiments, the calculating unit 15041 calculating reference data of the first data and the second data in the reference data region includes filtering the first data and the second data in a channel direction (the x direction) of the incomplete detector, to obtain channel-direction filtered first data and second data, and calculating reference data of the channel-direction filtered first data and second data at a reference data channel in the channel direction.

In some other embodiments, the calculating unit 15041 calculating reference data of the first data and the second data in the reference data region includes filtering the first data and the second data in a channel direction (the x direction) and a row direction (the z direction) of the incomplete detector, respectively, to obtain channel-direction filtered first data and second data and row-direction filtered first data and second data, calculating reference data of the channel-direction filtered first data and second data at a reference data channel in the channel direction, and reference data of the row-direction filtered first data and second data at a reference data row in the row direction, and obtaining the reference data of the first data and the second data in the reference data region using the reference data at the reference data channel in the channel direction and the reference data at the reference data row in the row direction.

In some embodiments, the first compensation unit 15042 compensating data in the third data corresponding to the detector missing portions by using reference data includes adding or multiplying the third data with the reference data, and filtering the added or multiplied data to obtain filtered data as the compensated third data.

In some other embodiments, the first compensation unit 15042 compensating data in the third data corresponding to the detector missing portions by using reference data includes adding or multiplying the third data with the reference data, and filtering the added or multiplied data in the channel direction and in the row direction, respectively, to obtain filtered data as the compensated third data.

In some other embodiments, as shown in FIG. 15, the second processing unit 1504 includes a fitting unit 15043 that fits first data and second data in a reference data region to obtain fitted data, and a second compensation unit 15044 that compensates data in third data corresponding to detector missing portions by using the fitted data to obtain compensated third data.

In some embodiments, the fitting unit 15043 fitting the first data and the second data in the reference data region includes filtering the first data and the second data in the channel direction of the incomplete detector, to obtain channel-direction filtered first data and second data, and fitting the channel-direction filtered first data and second data at the reference data channel in the channel direction to obtain the fitted data.

In some embodiments, the second compensation unit 15044 compensating data in the third data corresponding to the detector missing portions by using reference data includes replacing the third data of the reference data region with the fitted data, and filtering the replaced data to obtain filtered data as the compensated third data.

In the above embodiment, the reference data may be the difference or quotient between the first data and the second data in the reference data region.

In the above embodiment, the reference data region may include a channel of detector modules at the junction in a channel direction of the detector missing portions and the remaining portion of the incomplete detector, or one or more channels of detector modules from the junction in the channel direction to a central position in the channel direction of the incomplete detector, and/or, the reference data region includes a row of detector modules at the junction in a row direction of the detector missing portions and the remaining portion of the incomplete detector, or one or more rows of detector modules from the junction in the row direction to a central position in the row direction of the incomplete detector.

In the above embodiment, in some implementations, the reference data region includes a plurality of channels of detector modules from the junction in a channel direction of the detector missing portions and the remaining portion of the incomplete detector to a central position in the channel direction of the incomplete detector, and the reference data is one or more among an average value, a median, a maximum value and a minimum value of data corresponding to the plurality of channels of detector modules.

In the above embodiment, in some other implementations, the reference data region includes a plurality of rows of detector modules from the junction in a row direction of the detector missing portions and the remaining portion of the incomplete detector to a central position in the row direction of the incomplete detector, and the reference data is one or more among an average value, a median, a maximum value and a minimum value of data corresponding to the plurality of rows of detector modules.

In the embodiments of the present application, the incomplete detector is cross-shaped, triangular, a rhombus, fence-shaped, or I-shaped.

For the sake of simplicity, FIG. 15 only exemplarily illustrates the connection relationship or signal direction between various components or modules, but it should be clear to those skilled in the art that various related technologies such as a bus connection can be used. The various components or modules can be implemented by means of a hardware facility such as a processor or a memory, etc. The embodiments of the present application are not limited thereto.

The above embodiments merely provide illustrative descriptions of the embodiments of the present application. However, the present application is not limited thereto, and appropriate variations may be made on the basis of the above embodiments. For example, each of the above embodiments may be used independently, or one or more among the above embodiments may be combined.

According to the embodiments of the present application, by performing the two scans using the incomplete detector, and stitching and compensating the data obtained by the two scans, while reducing the total dose of X-rays, the integrity of the obtained data is ensured, and the image quality of the final obtained scanned image is maintained.

Embodiments of the present application provide an electronic device, including the computed tomography imaging apparatus 1500 as described in the embodiments of the second aspect, the content of which is incorporated herein. The electronic device may, for example, be a computer, a server, a workstation, a laptop, a smart phone, etc., but the embodiments of the present application are not limited thereto.

Figure 16:
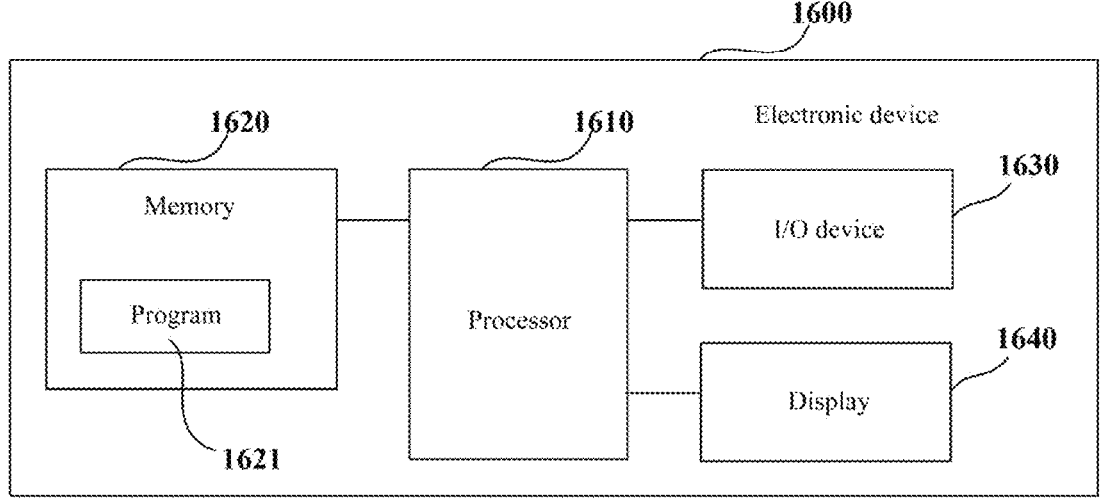
FIG. 16 is a schematic diagram of an electronic device according to an embodiment of the present application.

FIG. 16 is a schematic diagram of an electronic device according to an embodiment of the present application. As shown in FIG. 16, the electronic device 1600 may include: one or more processors (for example, a central processing unit (CPU)) 1610; and one or more memories 1620 coupled to the one or more processors 1610. The memory 1620 may store various data, and in addition, further store a program 1621 for information processing, and execute the program 1621 under the control of the processor 1610.

In some embodiments, functions of the computed tomography imaging apparatus 1500 are integrated into and implemented by the processor 1610. The processor 1610 is configured to implement the computed tomography imaging method according to the embodiments of the first aspect.

In some embodiments, the computed tomography imaging apparatus 1500 and the processor 1610 are configured separately. For example, the computed tomography imaging apparatus 1500 can be configured to be a chip that is connected to the processor 1610 and the functions of the computed tomography imaging apparatus 1500 can be implemented by means of the control of the processor 1610.

For example, the processor 1610 is configured to perform the following controls: pre-scanning an examined site by using an incomplete detector at a pitch factor of greater than 3 to obtain first data; axially scanning the examined site using the incomplete detector to obtain second data; stitching the first data and the second data to obtain third data; compensating the third data to obtain compensated third data; and performing image reconstruction by using the compensated third data to obtain a scanned image.

In addition, as shown in FIG. 16, the electronic device 1600 may further include: an input/output (I/O) device 1630 and a display 1640, etc. Functions of the above components are similar to those in the prior art, and are not repeated herein. It should be noted that the electronic device 1600 does not necessarily include all of the components shown in FIG. 16. In addition, the electronic device 1600 may further include components not shown in FIG. 16, for which reference may be made to related technology.

Embodiments of the present application further provide a computer-readable program, wherein when the program is executed in an electronic device, the program enables a computer to execute, in the electronic device, the computed tomography imaging method as described in the embodiments of the first aspect.

Embodiments of the present application further provide a storage medium that stores a computer-readable program, wherein the computer-readable program enables a computer to execute, in the electronic device, the computed tomography imaging method as described in the embodiments of the first aspect.

The above apparatus and method of the present application can be implemented by hardware, or can be implemented by hardware in combination with software. The present application relates to the foregoing type of computer-readable program. When executed by a logic component, the program causes the logic component to implement the foregoing apparatus or a constituent component, or causes the logic component to implement various methods or steps as described above. The present application further relates to a storage medium for storing the above program, such as a hard disk, a disk, an optical disk, a DVD, a flash memory, etc.

The method/apparatus described in view of the embodiments of the present application may be directly embodied as hardware, a software module executed by a processor, or a combination of the two. For example, one or more of the functional block diagrams and/or one or more combinations of the functional block diagrams shown in the drawings may correspond to either respective software modules or respective hardware modules of a computer program flow. The foregoing software modules may respectively correspond to the steps shown in the figures. The foregoing hardware modules can be implemented, for example, by firming the software modules using a field-programmable gate array (FPGA).

The software modules may be located in a RAM, a flash memory, a ROM, an EPROM, an EEPROM, a register, a hard disk, a portable storage disk, a CD-ROM, or any other form of storage medium known in the art. The storage medium may be coupled to a processor, so that the processor can read information from the storage medium and can write information into the storage medium. Alternatively, the storage medium may be a component of the processor. The processor and the storage medium may be located in an ASIC. The software module may be stored in a memory of a mobile terminal, and may also be stored in a memory card that can be inserted into a mobile terminal. For example, if a device (such as a mobile terminal) uses a large-capacity MEGA-SIM card or a large-capacity flash memory device, the software modules can be stored in the MEGA-SIM card or the large-capacity flash memory apparatus.

One or more of the functional blocks and/or one or more combinations of the functional blocks shown in the accompanying drawings may be implemented as a general-purpose processor, a digital signal processor (DSP), an application-specific integrated circuit (ASIC), a field-programmable gate array (FPGA) or other programmable logic devices, discrete gate or transistor logic devices, a discrete hardware assembly, or any appropriate combination thereof for implementing the functions described in the present application. The one or more functional blocks and/or the one or more combinations of the functional blocks shown in the accompanying drawings may also be implemented as a combination of computing devices, such as a combination of a DSP and a microprocessor, multiple microprocessors, one or more microprocessors in communication combination with a DSP, or any other such configuration.

The present application is described above with reference to specific embodiments. However, it should be clear to those skilled in the art that the foregoing description is merely illustrative and is not intended to limit the scope of protection of the present application. Various variations and modifications may be made by those skilled in the art according to the principle of the present application, and said variations and modifications also fall within the scope of the present application.

The invention claimed is:

1. A computed tomography imaging apparatus, characterized by comprising:
   a first scanning unit that pre-scans an examined site by using an incomplete detector at a pitch factor of greater than 3 to obtain first data, wherein the incomplete detector includes detector missing portions partial off-center detector modules of which are removed from a plurality of detector modules arranged in an array;
   a second scanning unit that axially scans the examined site using the incomplete detector to obtain second data;
   a first processing unit that stitches the first data and the second data to obtain third data;
   a second processing unit that compensates the third data to obtain compensated third data; and
   an image reconstruction unit that performs image reconstruction by using the compensated third data to obtain a scanned image, wherein the second processing unit includes a calculating unit that calculates reference data of the first data and the second data in a reference data region and a first compensation unit that compensates data of the third data corresponding to the detector missing portions by using the reference data to obtain the compensated third data.

2. The apparatus according to claim 1, wherein, a tube voltage used for a pre-scan is lower than that used for a conventional scan, and/or a tube current used for the pre-scan is lower than that used for a conventional scan.

3. The apparatus according to claim 1, wherein, an X-ray radiation dose used for a pre-scan is lower than that used for a conventional scan.

4. The apparatus according to claim 1, wherein the first processing unit stitching the first data and the second data comprises:
   upsampling the first data using an interpolation algorithm; and
   stitching the upsampled first data with the second data to obtain the third data.

5. The apparatus according to claim 1, wherein the calculating unit calculating the reference data of the first data and the second data in the reference data region comprises:
   filtering the first data and the second data in a channel direction of the incomplete detector to obtain channel-direction filtered first data and second data; and
   calculating reference data of the channel-direction filtered first data and second data at a reference data channel in the channel direction.

6. The apparatus according to claim 1, wherein the first compensation unit compensating the data of the third data corresponding to the detector missing portions by using the reference data comprises:

adding or multiplying the third data with the reference data; and filtering the added or multiplied data to obtain filtered data as the compensated third data.

7. The apparatus according to claim 1, wherein the calculating unit calculating the reference data of the first data and the second data in the reference data region comprises:

filtering the first data and the second data in a channel direction and a row direction of the incomplete detector, respectively, to obtain channel-direction filtered first data and second data and row-direction filtered first data and second data;

calculating reference data of the channel-direction filtered first data and second data at a reference data channel in the channel direction, and reference data of the row-direction filtered first data and second data at a reference data row in the row direction; and obtaining the reference data of the first data and the second data in the reference data region by using the reference data at the reference data channel in the channel direction and the reference data at the reference data row in the row direction.

8. The apparatus according to claim 1, wherein the first compensation unit compensating the data of the third data corresponding to the detector missing portions by using the reference data comprises:

adding or multiplying the third data with the reference data; and separately filtering the added or multiplied data in a channel direction and a row direction to obtain filtered data as the compensated third data.

9. The apparatus according to claim 1, wherein the incomplete detector comprises detector missing portions partial off-center detector modules of which are removed from a plurality of detector modules arranged in an array, and the second processing unit comprises:

a fitting unit that fits the first data and the second data in a reference data region to obtain fitted data; and a second compensation unit that compensates data of the third data corresponding to the detector missing portions by using the fitted data to obtain the compensated third data.

10. The apparatus according to claim 9, wherein the fitting unit fitting the first data and the second data in the reference data region comprises:

filtering the first data and the second data in a channel direction of the incomplete detector to obtain channel-direction filtered first data and second data; and fitting the channel-direction filtered first data and second data at a reference data channel in the channel direction to obtain fitted data.

11. The apparatus according to claim 9, wherein the second compensation unit compensating the data of the third data corresponding to the detector missing portions by using the fitted data comprises:

replacing the third data of the reference data region with the fitted data; and filtering the replaced data to obtain filtered data as the compensated third data.

12. The apparatus according to claim 1, wherein, the reference data region comprises a channel of detector modules located at a junction in a channel direction of the detector missing portions and the remaining portion of the incomplete detector, or one or more channels of detector modules from the junction in the channel direction to a central position in the channel direction of the incomplete detector, and/or, the reference data region comprises a row of detector modules located at the junction in a row direction of the detector missing portions and the remaining portion of the incomplete detector, or one or more rows of detector modules from the junction in the row direction to a central position in the row direction of the incomplete detector.

13. The apparatus according to claim 1, wherein, the reference data region comprises a plurality of channels of detector modules from a junction in a channel direction of the detector missing portions and the remaining portion of the incomplete detector to a central position in the channel direction of the incomplete detector, and the reference data is one or more among an average value, a median, a maximum value and a minimum value of data corresponding to the plurality of channels of detector modules; and/or, the reference data region comprises a plurality of rows of detector modules from the junction in a row direction of the detector missing portions and the remaining portion of the incomplete detector to a central position in the row direction of the incomplete detector, and the reference data is one or more among an average value, a median, a maximum value and a minimum value of data corresponding to the plurality of rows of detector modules.

14. The apparatus according to claim 1, wherein, the reference data is the difference or quotient between the first data and the second data in the reference data region.

15. The apparatus according to claim 1, wherein the incomplete detector is cross-shaped, triangular, a rhombus, fence-shaped, or I-shaped.

16. A computed tomography imaging method, characterized by comprising:

pre-scanning an examined site by using an incomplete detector at a pitch factor of greater than 3 to obtain first data, wherein the incomplete detector includes detector missing portions partial off-center detector modules of which are removed from a plurality of detector modules arranged in an array;

axially scanning the examined site using the incomplete detector to obtain second data;

stitching the first data and the second data to obtain third data;

calculating reference data of the first data and the second data in a reference data region located at a junction of the detector-missing portions and remaining portions of the incomplete detector;

compensating data of the third data corresponding to the detector-missing portions by using the reference data to obtain compensated third data; and performing image reconstruction by using the compensated third data to obtain a scanned image.

* * * * *